United States Patent [19]

Sakurai et al.

[11] Patent Number: 4,772,795

[45] Date of Patent: Sep. 20, 1988

[54] UV-STERILIZER FOR A DENTAL IMPLEMENT SUCH AS A REAMER AND DRILL

[75] Inventors: Masatoshi Sakurai, Sakado; Akio Shigeno, Tokyo; Yoshihiko Noguchi, Yokohama, all of Japan

[73] Assignee: Kyowairika Co., Ltd., Kanagawa, Japan; a part interest

[21] Appl. No.: 28,477

[22] Filed: Mar. 20, 1987

[51] Int. Cl.[4] .............................................. H01J 37/20
[52] U.S. Cl. .............................. 250/455.1; 250/504 R; 250/492.1
[58] Field of Search ............. 250/455.1, 492.1, 504 R, 250/503.1, 494.1

[56] References Cited

U.S. PATENT DOCUMENTS

| | | | |
|---|---|---|---|
| 2,074,909 | 3/1937 | Herzig et al. | 250/503.1 |
| 3,433,579 | 3/1969 | Runnion | 250/455.1 |
| 4,412,134 | 10/1983 | Herold et al. | 250/455.1 |

FOREIGN PATENT DOCUMENTS 2929805  1/1981  Fed. Rep. of Germany ... 250/455.1

Primary Examiner—Carolyn E. Fields
Assistant Examiner—John A. Miller
Attorney, Agent, or Firm—Koda and Androlia

[57] ABSTRACT

A UV-sterilizer for a dental implement such as a reamer or drill permitting rapid and perfect irradiation and easy operation, comprising a sterilizer housing, a holder tube made of a transparent quartz glass tube and a plurality of UV-sterilizer lamps, both the holder tube and UV-sterilizer lamps being disposed within the sterilizer housing, wherein the sterilizer housing is provided with reflector plates and a gate mechanism substantially similar to a photographic diaphragm mechanism on an open end of the holder tube.

3 Claims, 5 Drawing Sheets

UV-STERILIZER FOR A DENTAL IMPLEMENT SUCH AS A REAMER AND DRILL

BACKGROUND OF THE INVENTION

1. Field of the Invention

The present invention relates to a UV-sterilizer for dental implements such as a reamer and drill and, more particularly, to such UV-sterilizer suitable for easily, simply and effectively sterilizing shaft- or rod-like implements used to ream and drill human teeth, for example, with an implement known in the industry as an air turbine handpiece.

2. Prior Art

For sterilization of the dental reamer or drill such as the above-mentioned air turbine handpiece, there has usually been employed a method in which the dental implement is immersed into a solution of formalin for sterilizing purposes. However, this method is unsuitable for sterilization of a dental implement such as a handpiece which must be frequently sterilized, since this method requires a relatively long duration of time for effective sterilization. As an expedient means for sterilization, a storage cabinet has also been used, although the cabinet itself is not a sterilizer but merely serves to keep the dental implements under a hygienic condition. The cabinet comprises a rectangular or cylindrical box-like container which includes therein, in turn, racks and UV-sterilizer lamps. However, this is a storage cabinet by nature and is not a sterilizer so that such a cabinet can not provide an adequate effect of sterilization and requires a relatively long duration of time even for inadequate sterilization. In addition, the dental implements are plated on the respective racks in order to be exposed to UV-rays directed from above or other locations for sterilization and, therefore, UV-rays will be intercepted by the wire material of the racks if the cabinet is provided with a plurality of racks. In this manner, the dental implements partially remain unexposed to UV-rays and this inconvenience also leads to inadequate sterilization.

SUMMARY OF THE INVENTION

An object of the present invention is, in view of the problems as set forth above, to provide means adapted to afford an adequate effect of sterilization by perfectly exposing dental implements such as a reamer or drill to UV-rays emitted from the UV-sterilizer lamps without even partially intercepting the UV-rays.

Another object of the present invention is to provide means adapted to afford further improved sterilizing effect through diffused reflection of the UV-rays emitted from the UV-sterilizer lamps such that the dental implements can be exposed, even on the recesses and rear sides thereof, to the UV-rays as perfectly as possible.

A further object of the present invention is to provide means permitting the sterilizing operation to be rapidly and easily done.

These objects are achieved, in accordance with the present invention, by a UV-sterilizer for dental implements such as a reamer or drill comprising a sterilizer housing, a holder tube made of a transparent quartz glass tube disposed within the sterilizer housing to hold the dental implement inserted thereinto, and a plurality of UV-sterilizer lamps disposed closely around the holder tube, characterized in that the sterilizer housing containing therein the holder tube made of transparent quartz glass tube is provided inside with reflector plates serving to cause a diffused reflection of the UV-rays emitted from the UV-sterilizer lamps and provided in a front wall in alignment with the holder tube made of transparent quartz glass tube with a gate mechanism substantially similar to a photographic diaphragm mechanism. In this way it is possible to perfectly expose the dental implements to the UV-rays emitted from the UV-sterilizer lamps without intercepting these UV-rays even partially and to expose the dental implements even on the recesses and rear sides thereof to the UV-rays as perfectly as possible through diffused reflection of the UV-rays emitted from the UV-sterilizer lamps so that a further improved effect of sterilization may be achieved.

Additionally, the sterilizer constructed in accordance with the present invention can be simply operated, since the desired effect of sterilization can be achieved merely by inserting the dental implement into the holder tube. The duration of time needed for the desired sterilization is significantly reduced, making it possible to achieve a rapid sterilization operation, since the sterilizer lamps are disposed closely around the holder tube made of a transparent quartz glass tube, i.e., the sterilizer lamps are adjacent to the dental implements to be sterilized so as to provide correspondingly intense sterilizing rays. Thus, a sterilizing effect sufficiently high to be effective for sterilization of various viruses as AIDS.

Furthermore, a gate mechanism substantially similar to the photographic diaphragm mechanism serves to shut off any leakage of the UV-rays emitted from the UV-sterilizer lamps and thereby protects the eyes of the operators from such leakage. Moreover, the UV-sterilizer of the present invention is arranged so that the UV-sterilizer lamps are energized only after the gate mechanism has been closed and, accordingly, high operational safety is assured.

BRIEF DESCRIPTION OF THE DRAWINGS

A preferred embodiment of the present invention is illustrated in the accompanying drawings in which.

DETAILED DESCRIPTION OF THE INVENTION

The present invention will be described in more detail with respect to the accompanying drawings.

Figure 1:
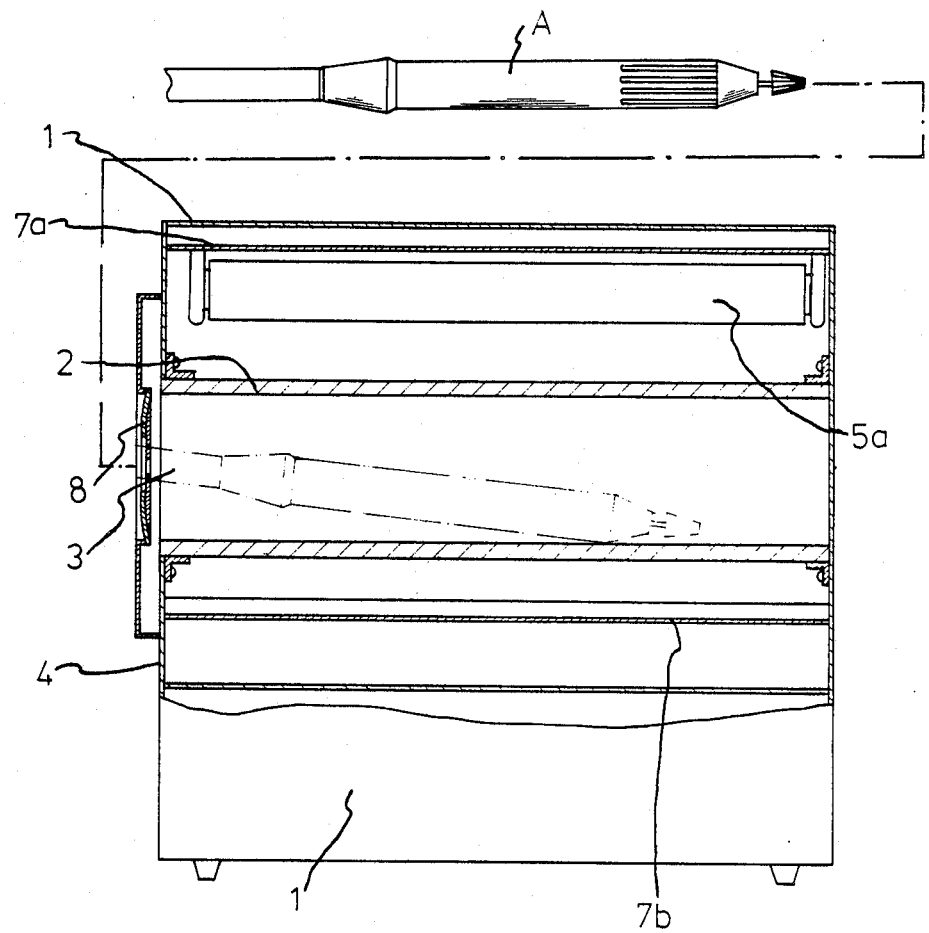
FIG. 1 is a partially broken side view illustrating a manner in which a dental implement is inserted into the holder tube.
Figure 2:
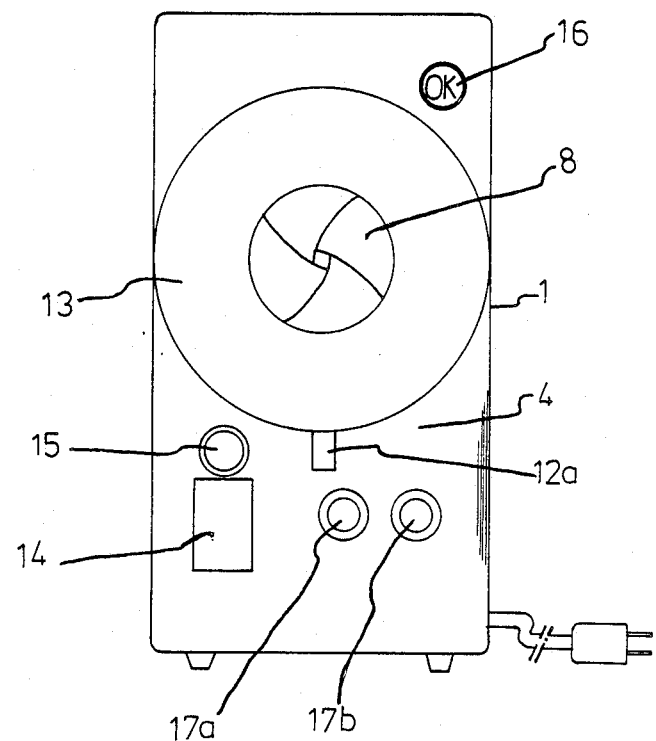
FIG. 2 is a front view illustrating a sterilizer according to the present invention.
Figure 3:
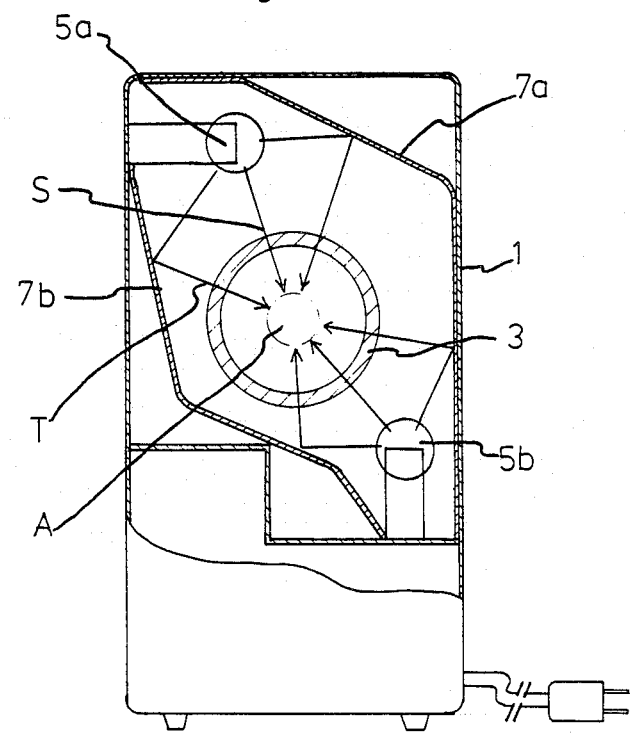
FIG. 3 is a view similar to FIG. 2, but as partially broken away.

Referring to FIGS. 1 through 3, reference numeral 1 designates a sterilizer housing containing therein a holder tube 2 made of a transparent quartz glass tube having an inside diameter appropriately dimensioned for insertion of a dental implement A such as a so-called air turbine handpiece and being excellent in UV-transmissivity. In this case, the holder tube 2 is disposed within the sterilizer housing 1 with one open end 3 of the holder tube 2 being adjacent a front side 4 of the sterilizer housing 1 so that the dental implement A may be easily and rapidly inserted into and withdrawn from the holder tube 2.

Reference numerals 5a and 5b designate cylindrical UV-sterilizer lamps fixedly disposed within the sterilizer housing 1 closely around the holder tube 2 so as to be opposed to each other across the holder tube 2. UV-rays emitted from these UV-sterilizer lamps 5a and 5b are directed through the cylindrical holder tube 2 made of a transparent quartz glass tube into which the dental implement A inserted and held therein. The sterilizer housing 1 is further provided therein with diffused reflection plates 7a and 7b made of aluminum so as to surround the cylindrical holder tube 2 and cylindrical UV-sterilizer lamps 5a and 5b so as to effect the desired diffused reflection of the UV-rays or reflected UV-rays emitted from the respective UV-sterilizer lamps 5a and 5b.

In this embodiment, the reflection plates 7a and 7b comprise substantially L-shaped plates, respectively, curved at appropriate angles so that their combined central portions are curved at larger angles opposed to each other across the cylindrical holder tube 2. The reflection plates 7a and 7b thus combined with each other present a cross-section substantially corresponding to a parallelogram and the UV-sterilizer lamps 5a and 5b are disposed inside the associated smaller angles of the parallelogram.

A gate mechanism 8 substantially similar to the diaphragm mechanism of a photographic camera is mounted in a front wall of the sterilizer housing 1 in alignment with an open end 3 of the holder tube 2 made of a transparent quartz glass tube.

Figure 4A:
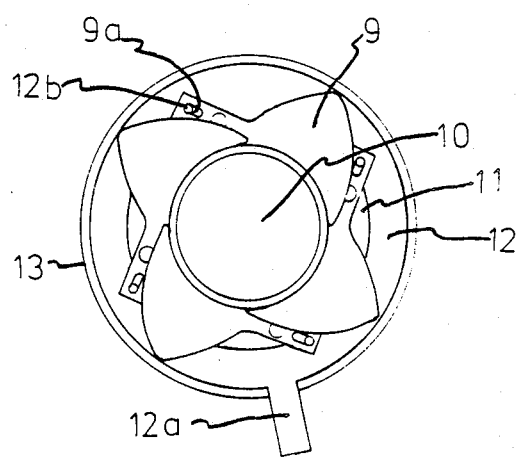
FIG. 4a is a diagram illustrating an opened gate mechanism as viewed from the rear side.
Figure 4B:
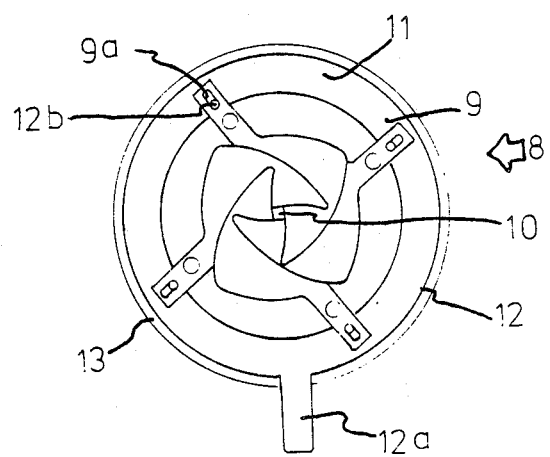
FIG. 4b is a diagram similar to FIG. 4a, but illustrating the closed gate mechanism as viewed from the rear side.

FIGS. 4a and 4b illustrate this gate mechanism 8 as viewed from the rear side. As shown, the gate mechanism 8 comprises a plurality of sector-shaped blades, for example, made of stainless sheets (four blades are shown) overlapping one another so that the overlapped assembly centrally defines an insertion area 10. These sector-shaped blades 9 are pivotally supported at their roots by a common inner ring 11 and their portions extending beyond the respective pivots outward are provided with slots 9a into which associated pins 12b of an outer ring 12 are engaged. Reference numeral 13 designates an outer frame. The outer ring 12 includes an operating lever 12a extending through the outer frame outwardly and this operating lever 12a may be operated to rotate the outer ring 12. The inner ring 11 is stationary.

FIG. 4a shows the gate mechanism 8 completely opened while FIG. 4b shows the gate mechanism 8 closed with the insertion area 10 remaining slightly opened. Rotation of the outer ring 12 within the outer frame 13 through operation of the lever 12a causes the pins 12b to urge the portions of the respective sector-shaped blades 9 extending beyond the associated pivots so as to be rotated in a same direction as the outer ring 12 circumferentially moves while portions of the respective sector-shaped blades radially extending inwardly with respect to the pivots are rotated in a direction opposite to the direction in which the outer ring 12 circumferentially moves.

By rotating the sector-shaped blades 9 in this manner to change the overlapping condition thereof, it is possible to control size of the insertion area 10 which is certainly defined by the overlapped assembly of the blades 9.

As seen in FIG. 2, the sterilizer housing 1 is provided on the front 4 with, in addition to the gate mechanism 8, a source switch 14, a lamp 15 indicating a state of the source switch 14, an OK lamp switch 16 and lamps 17a and 17b indicating that the sterilizer lamps 5a and 5b have been energized.

Figure 5:
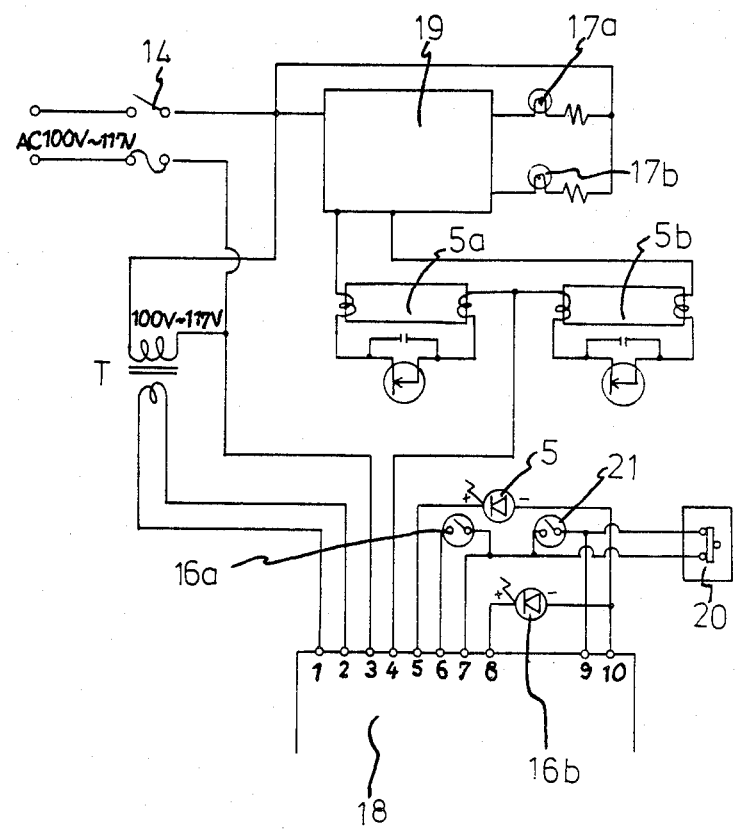
FIG. 5 is a wiring diagram of the present invention.

FIG. 5 is a wiring diagram for these components, in which reference numeral 18 designates an IC control circuit functioning as a timer, reference numeral 19 designates a stabilizer for the sterilizer lamps, reference numeral 20 designates a slidable reset switch mounted on the rear side of the housing 1 and reference numeral 21 designates a switch operatively associated with the gate mechanism 8.

Now operation of the sterilizer constructed as has been described hereinabove will be described.

To sterilize a dental implement such as an air turbine handpiece which has been used for a particular dental treatment, a source plug is inserted into a plug socket and the source switch 14 is turned on. The lamp 15 is thereby energized, indicating that the source switch 14 has been turned on.

In this state, even if the gate mechanism 8 and, therefore, the switch 21 operatively associated with the gate mechanism 8 are also closed as seen in FIG. 2, the sterilizer lamps 5a and 5b are still not energized, since a switching member 16a of the OK lamp switch 16 is in an open position.

Then, the gate mechanism 8 is fully opened by manually operating the lever 12a and the dental implement A to be sterilized is inserted into the holder tube 2 made of a transparent quartz tube from the one open end 3 thereof.

When the gate mechanism 8 is closed, the sector-shaped blades 9 are closed leaving an area corresponding to a cross-section area of a cord connected to the dental implement A. Thus, no gap remains around the implement A and there is no leakage of the UV-rays from the interior of the stabilizer housing. The switch 21 operatively associated with the gate mechanism is opened as the gate mechanism 8 is fully opened and closed again as the gate mechanism is closed again.

After the dental implement A to be sterilized has been inserted into the holder tube 2 as mentioned above, the OK lamp switch 16 is turned on. The lamp 16b is lit, indicating that the switch 16 has been turned on, and the UV-sterilizer lamps 5a and 5b are lit.

Consequently, the UV-rays emitted from the respective UV-sterilizer lamps 5a and 5b are directed as indicated by the arrow S, through the holder tube 2 made of a transparent quartz glass tube onto the outer peripheral surface of the implement A inserted thereinto in order to effect the desired sterilization. The holder tube 2 is made of transparent quartz glass and, therefore, the irradiation of the UV-rays is effectively achieved without being intercepted by the holder tube 2. The UV-rays emitted from the respective UV-sterilizer lamps 5a and 5b are partially subjected to a diffused reflection on the reflector plates 7 made of aluminum, resulting in that the dental implement A is exposed to UV-rays coming from every direction, as indicated by the arrow T. Consequently, the dental implement A can be irradiated with the UV-rays even in recesses and the rear side portions thereof as perfectly as possible, even if the dental implement A has a somewhat irregular surface and other members on its rear side, and thus adequate sterilization is achieved.

Upon switching on of the OK lamp switch 16, a timer included in the IC control circuit 18 is activated so that, after a predetermined time (approximately 60 sec) required for the irradiation of the UV-rays has elapsed, the lamp 16b associated with the OK lamp switch 16 begins to flicker, indicating that the desired sterilization operation has been completed.

It will be obvious that the interior of the housing can not be seen from the exterior after the gate mechanism 8 has been closed. Accordingly, there is a danger that, if any one of the sterilizer lamps 5a and 5b has a disconnection fault, imperfect irradiation occurs without be noticed. To avoid such inconvenience, it is assured in accordance with the present invention that, when the sterilizer lamps 5a and 5b are properly lit, the associated lamps 17a and 17b are also lit, indicating there is no disconnection fault concerning both the lamps 5a and 5b.

After the irradiation of UV-rays for the necessary duration of time, the gate mechanism 8 is opened and the dental implement A is removed from the holder tube 2. In this manner, sterilization of a dental implement A such as an air turbine handpiece is completed.

The sterilizer lamps 5a and 5b are deenergized as the switch 21 operatively associated with the gate mechanism 8 is opened when the latter is opened after the time required for irradiation has elapsed. Alternatively, the sterilizer lamps 5a and 5b may be automatically deenergized by the timer.

By slidably closing the reset switch 20, it is possible to maintain the sterilizer lamps 5a and 5b energized, independently of the time or the switch 21 operatively associated with the gate mechanism 8, enabling irradiation without any time limit to be achieved under a particular situation.

What is claimed is:

1. A UV-sterilizer for dental implements of the type including a reamer or drill, said UV-sterilizer comprising a sterilizer housing, a holder tube made of a transparent quartz glass tube disposed within said sterilizer housing to hold the dental implement inserted thereinto, and a plurality of UV-sterilizer lamps disposed in close proximity around said holder tube, and further characterized in that the sterilizer housing containing therein said holder tube made of transparent quartz glass tube is provided thereinside with reflector plates disposed to cause a diffused reflection of UV-rays emitted from the UV-sterilizer lamps and provided in a front wall in alignment with said holder tube made of transparent quartz glass tube is a gate means substantially similar to a photographic diaphragm mechanism.

2. A UV-sterilizer for a dental implement as defined in claim 1, wherein the gate means controls an ON-/OFF switch disposed in an energization control circuit for the UV-sterilizer lamps.

3. A UV-sterilizer for a dental implement as defined in claim 1, wherein the UV-sterilizer lamps are energized through an OK lamp switch mounted on a front surface of the sterilizer housing.

* * * * *